(12) United States Patent
Hawthorne et al.

(10) Patent No.: US 7,659,734 B2
(45) Date of Patent: Feb. 9, 2010

(54) SEMICONDUCTOR INSPECTION SYSTEM AND APPARATUS UTILIZING A NON-VIBRATING CONTACT POTENTIAL DIFFERENCE SENSOR AND CONTROLLED ILLUMINATION

(75) Inventors: Jeffrey Alan Hawthorne, Decatur, GA (US); M. Brandon Steele, Decatur, GA (US); Yeyuan Yang, Marietta, GA (US); Mark Schulze, Austin, TX (US)

(73) Assignee: Qcept Technologies, Inc., Atlanta, GA (US)

( * ) Notice: Subject to any disclaimer, the term of this patent is extended or adjusted under 35 U.S.C. 154(b) by 399 days.

(21) Appl. No.: 11/715,149

(22) Filed: Mar. 7, 2007

(65) Prior Publication Data

US 2008/0217530 A1 Sep. 11, 2008

(51) Int. Cl.
*G01R 31/26* (2006.01)
(52) U.S. Cl. .................................................... 324/719
(58) Field of Classification Search ............. 324/158.1, 324/500, 520, 750–762, 765–767; 382/149, 382/274; 356/432, 433, 445
See application file for complete search history.

(56) References Cited

U.S. PATENT DOCUMENTS

| | | | |
|---|---|---|---|
| 4,166,974 A | 9/1979 | Vermeers |
| 4,295,092 A | 10/1981 | Okamura |
| 4,481,616 A | 11/1984 | Matey |
| 4,973,910 A | 11/1990 | Wilson |
| 5,087,533 A | 2/1992 | Brown |
| 5,136,247 A | 8/1992 | Hansen |
| 5,214,389 A | 5/1993 | Cao et al. |
| 5,217,907 A | 6/1993 | Bulucea et al. |
| 5,218,362 A | 6/1993 | Mayes et al. |
| 5,270,664 A | 12/1993 | McMurtry et al. |
| 5,272,443 A | 12/1993 | Winchip et al. |

(Continued)

FOREIGN PATENT DOCUMENTS

DE   297 509 A5   1/1992

(Continued)

OTHER PUBLICATIONS

Baumgartner, et al., "Micro Kelvin probe for local work-function measurements", Review of Scientific Instrumetns, May 1988, USA; vol. 59, No. 5, pp. 802-805, XP0022922442, ISSN: 0034-6748 (abstract; fig. 4, chapter "V. Results").

(Continued)

*Primary Examiner*—Ha Tran T Nguyen
*Assistant Examiner*—Trung Q Nguyen
(74) *Attorney, Agent, or Firm*—Foley & Lardner LLP

(57) ABSTRACT

A method and system for identifying a defect or contamination on the surface of a semiconductor or in a semiconductor. The method and system involves providing a semiconductor with a surface, such as a semiconductor wafer, providing a non-vibrating contact potential difference sensor, providing a source of illumination with controllable intensity or distribution of wavelengths, using the illumination source to provide controlled illumination of the surface of the wafer under or near the non-vibrating contact potential sensor probe tip, using the non-vibrating contact potential difference sensor to scan the wafer surface during controlled illumination, generating data representative of changes in contact potential difference across the wafer surface, and processing that data to identify a pattern characteristic of a defect or contamination.

29 Claims, 5 Drawing Sheets

U.S. PATENT DOCUMENTS

| | | | |
|---|---|---|---|
| 5,278,407 A | 1/1994 | Ikebe et al. |
| 5,293,131 A | 3/1994 | Semones et al. |
| 5,315,259 A | 5/1994 | Jostlein |
| 5,369,370 A | 11/1994 | Stratmann et al. |
| 5,381,101 A | 1/1995 | Bloom et al. |
| 5,460,684 A | 10/1995 | Saeki et al. |
| 5,517,123 A | 5/1996 | Zhao et al. |
| 5,546,477 A | 8/1996 | Knowles et al. |
| 5,583,443 A | 12/1996 | McMurtry et al. |
| 5,723,980 A | 3/1998 | Haase et al. |
| 5,723,981 A | 3/1998 | Hellemans et al. |
| 5,773,989 A | 6/1998 | Edelman et al. |
| 5,974,869 A | 11/1999 | Danyluk et al. |
| 5,977,788 A | 11/1999 | Lagowski |
| 6,011,404 A | 1/2000 | Ma et al. |
| 6,037,797 A | 3/2000 | Lagowski et al. |
| 6,091,248 A | 7/2000 | Hellemans et al. |
| 6,094,971 A | 8/2000 | Edwards et al. |
| 6,097,196 A | 8/2000 | Verkuil et al. |
| 6,114,865 A | 9/2000 | Lagowski et al. |
| 6,127,289 A | 10/2000 | Debusk |
| 6,139,759 A | 10/2000 | Doezema et al. |
| 6,198,300 B1 | 3/2001 | Doezema et al. |
| 6,201,401 B1 | 3/2001 | Hellemans et al. |
| 6,232,134 B1 | 5/2001 | Farber et al. |
| 6,255,128 B1 | 7/2001 | Chacon et al. |
| 6,265,890 B1 | 7/2001 | Chacon et al. |
| 6,517,669 B2 | 2/2003 | Chapman |
| 6,520,839 B1 | 2/2003 | Gonzalez-Martin et al. |
| 6,538,462 B1 | 3/2003 | Lagowski et al. |
| 6,546,814 B1 | 4/2003 | Choe et al. |
| 6,551,972 B1 | 4/2003 | Lei et al. |
| 6,597,193 B2 | 7/2003 | Lagowski et al. |
| 6,664,546 B1 | 12/2003 | McCord et al. |
| 6,664,800 B2 | 12/2003 | Chacon et al. |
| 6,679,117 B2 | 1/2004 | Danyluk et al. |
| 6,680,621 B2 | 1/2004 | Savtchouk et al. |
| 6,711,952 B2 | 3/2004 | Leamy et al. |
| 6,717,413 B1 | 4/2004 | Danyluk et al. |
| 6,771,091 B2 | 8/2004 | Lagowski et al. |
| 6,791,310 B2 | 9/2004 | Smith |
| 6,803,241 B2 | 10/2004 | Eom et al. |
| 6,849,505 B2 | 2/2005 | Lee et al. |
| 6,858,089 B2 | 2/2005 | Castrucci |
| 6,929,581 B2 | 8/2005 | Sugimura |
| 7,019,654 B2 | 3/2006 | Danyluk et al. |
| 7,084,661 B2 | 8/2006 | Thompson et al. |
| 2002/0140564 A1 | 10/2002 | Danyluk et al. |
| 2002/0186036 A1 | 12/2002 | Smith |
| 2003/0052374 A1 | 3/2003 | Lee et al. |
| 2003/0129776 A1 | 7/2003 | Eom et al. |
| 2003/0139838 A1 | 7/2003 | Marella |
| 2003/0164942 A1 | 9/2003 | Take |
| 2003/0175945 A1 | 9/2003 | Thompson et al. |
| 2004/0029131 A1 | 2/2004 | Thompson et al. |
| 2004/0057497 A1 | 3/2004 | Lagowski et al. |
| 2004/0058620 A1 | 3/2004 | Gotkis et al. |
| 2004/0070355 A1 | 4/2004 | Ogura |
| 2004/0105093 A1 | 6/2004 | Hamamatsu et al. |
| 2004/0134515 A1 | 7/2004 | Castrucci |
| 2004/0152250 A1 | 8/2004 | Steele et al. |
| 2004/0241891 A1 | 12/2004 | Scott et al. |
| 2005/0162178 A1 | 7/2005 | Steele et al. |

FOREIGN PATENT DOCUMENTS

| | | |
|---|---|---|
| EP | 1 039 277 A1 | 9/2000 |
| EP | 1 304 463 B1 | 9/2005 |
| WO | WO 01/90730 A2 | 11/2001 |

OTHER PUBLICATIONS

Castaldini et al., "Scanning Kelvin probe and surface photovoltage analysis of multicrystalline silicon", Materials Science and Engineering B., Elsevier Sequoia, Lausanne, CH; vol. 91-92, Apr. 30, 2002, pp. 234-238, XP004355534, ISSN: 0921-5107 (chapters "2.2 Scanning Kelvin probe: and 4.2 Scanning Kelvin probe analyses").

Castaldini et al., "Surface analyses of polycrystalline and Cz-Si wafers", Solar Energy Materials and Solar Cells, Elsevier Science Publishers, Amsterdam, NL; vol. 72, No. 1-4, Apr. 2002, pp. 425-432, XP004339790, ISSN: 0927-0248 (whole document).

Danyluk., "Non-vibrating contact potential imaging for semiconductor fabrication", Semicon West 2003, 'Online!, Jul. 14, 2003, pp. 1-15, XP002292443, retrieved from the internet: ,URL:http://dom.semi.org/web/wFiles.nsf/Lookup/TIS18_QceptTechnologiesInc/$file/TIS18%20QceptTechnologiesInc.Alternate.pdf. 'retrieved on Aug. 13, 2004 (whole document).

Korach et al., "Measurement of perfluoropolyether lubricant thickness on a magnetic disk surface", Applied Physics Letters, American Institute of Physics, New York, NY, US; vol. 79, No. 5, Jul. 30, 2001, pp. 698-700, XP012029958, ISSN: 0003-6951 (p. 699, left column; fig. 2).

Lagel et al., "A novel detection system for defects and chemical contamination in semiconductors based upon the scanning Kelvin probe", $14^{th}$ International Vacuum Congress (IVC-14). $10^{th}$ International Conference on Solid Surfaces (ICS-10). $5^{th}$ International Conference on Nanometre-Scale Science and Technology (NANO-5). $10^{th}$ International Conference on Quantitative Surface Analysis; vol. 433-435, pp. 622-626, XP002292441, Surface Science, Aug. 2, 1999, Elsevier, NL, ISSN: 003906028 (whole document).

Reid, Jr., "Surface Characterization of Hard Disks Using Non-Contact Work Function Capacitance Probe," A Thesis Presented to the Academic Faculty in Partial Fulfillment of the Requirements for the Degree of Master of Science in Mechanical Engineering, Georgia Institute of Technology, Jun. 1986.

Ren et al., "Scanning Kelvin Microscope: a new method for surface investigations" 8. Arbeitstatgung Angewandte Oberflachenanalytik 'AOFA 8' ('Applied Surface Analysis'), Kaiserslautern, DE, Sep. 5-8, 1994; vol. 353, No. 3-4, pp. 303-306, XP009035181, Fresenius' Jounal of Analytical Chemistry, Oct. 1995, Springer-Verlag, DE, ISSN: 0937-0633 (p. 304, right column; fig. 1).

Scruton et al., "A High Resolution Probe for Scanning Electrostatic Potential Profiles Across Surfaces"; Journal of Physics E: Scientific Instruments (May 1973), pp. 472-474; vol. 6, No. 5, Printed in Great Britain.

Yang et al., "Kelvin probe study on the perfluoropolyether film on metals", Tribology Letters, 2001, Kluwer Academic/Plenum Publishers, USA, vol. 10, No. 4, pp. 211-216, XP009035197, ISSN: 1023-8883 (p. 211-p. 212).

Yano et al., "Nonvibrating contact potential difference probe measurement of a nanometer-scale lubricant on a hard disk", Journal of Tribology, American Society of Mechanical Engineers, New York, NY, US; vol. 121, No. 4, Oct. 1999, pp. 980-983, XP008031092, ISSN: 0742-4787 (pp. 980-981, fig. 4, first ref. on p. 983).

SEMICONDUCTOR INSPECTION SYSTEM AND APPARATUS UTILIZING A NON-VIBRATING CONTACT POTENTIAL DIFFERENCE SENSOR AND CONTROLLED ILLUMINATION

FIELD OF THE INVENTION

The present invention is directed to methods and systems for the inspection of semiconductors and semiconductor surfaces. More particularly, the present invention is directed to a method and system for the characterization of non-uniformities through the use of a non-vibrating contact potential difference sensor in combination with a controllable illumination source to image and visualize the contact potential difference of the wafer surface.

BACKGROUND OF THE INVENTION

The function, reliability and performance of semiconductor devices depend on the use of semiconductor materials and surfaces which are clean and uniform. Billions of dollars and countless man-hours have been spent developing, characterizing, and optimizing systems and processes for fabricating and processing semiconductor materials. A primary goal of this activity has been the fabrication of materials and surfaces that are extremely clean and that have properties that are uniform, or vary uniformly, across the entire wafer. In order to characterize and optimize these processes it is necessary to be able to inspect and measure surface or bulk cleanliness and uniformity. For real-time process control, it is necessary to be able to make many measurements across a surface at high speed, and to do so in a manner that does not damage or contaminate the semiconductor surface. It is also highly desirable to be able to detect or classify multiple different types of non-uniformities or contaminants.

Many different technologies and systems have been used to measure surface or bulk properties of semiconductors. Many of these systems are highly sensitive to specific bulk or surface characteristics, such as metallic contamination, but these systems are often slow, destructive, or make measurements at only a few points. These systems may also be limited in the types of measurements they can make or defects that they can detect. For example, a system which detects metal contamination may not be able to detect organic contamination, a system which can detect particles may not be able to detect sub-monolayer contaminants, or a system capable of making precise measurements at one or more points on the wafer may not be fast enough to measure all points on a wafer at production speeds.

One known method of measuring or characterizing the condition of a surface is the vibrating Kelvin probe, sometimes called the Kelvin-Zisman probe. The Kelvin probe is a sensor that measures Contact Potential Difference (CPD). CPD is the difference in work function, or surface potential, of two conductive materials which are electrically connected. The Kelvin sensor consists of a conductive probe which is electrically connected to the surface to be measured. The probe is positioned close to the surface so that a capacitor is formed between the probe tip and the surface. A potential difference (voltage) results from the CPD between the probe tip and the surface. The probe tip is positioned at a point above the surface and then vibrated perpendicular to the surface so that the capacitance between the probe tip and the surface varies with time. This varying capacitance results in a time-varying current into the probe tip which is proportional to the voltage between the probe tip and the surface. This current is amplified to facilitate detection, and a variable bias voltage, sometimes called a backing voltage, is applied to the probe such that the time varying current goes to zero. When the current is zero, the bias voltage is equal and opposite to the CPD, so the CPD is determined. Many variations of the Kelvin probe have been developed. These include the Monroe probe, which vibrates a shutter in front of the probe tip instead of vibrating the tip itself; and scanning probes which make vibrating measurements at a series of points across a surface by stepping from one point to the next or moving slowly while the probe is vibrated. For relatively high-speed scanning, the probe can be operated with a fixed, or no, bias voltage and the magnitude of the probe current can be calibrated and converted to surface potential values. In all cases the signal is generated by varying the capacitance between the probe tip and the surface using vibration.

Kelvin probes are very useful in the characterization of many surfaces, including semiconductor surfaces. The Kelvin probe is useful because the work function of a surface, and resulting surface potential and CPD, are very sensitive to a wide range of surface conditions that can affect semiconductor device quality; such as contamination, surface chemistry, atomic surface roughness and surface charging. However, the Kelvin probe is essentially a point measurement technique. Although multiple measurements can be made at different points on a surface, or a series of adjacent points can be measured in series, it is difficult to measure more than a few points per second. Generating high resolution images of whole semiconductor wafers is a slow and time consuming process that is not well-suited to real-time process control applications.

A second method of characterizing a semiconductor utilizes Surface Photo Voltage (SPV). The electrical potential of a semiconductor surface is often sensitive to illumination with specific frequencies of light. A semiconductor surface, or an interface between a semiconductor and another material, will typically result in surface or interface-specific electron energy states. These states can cause surface charging and the formation of electric fields near the surface. This phenomenon of changing electrical potential near a semiconductor surface is known as band bending. Illumination of the semiconductor surface with super-bandgap wavelengths of light, and the subsequent generation, drift and recombination of carriers, act to reduce the level of band bending. Illumination of the semiconductor surface with sub-bandgap illumination can cause the population and depopulation of surface states that will also affect surface charging, band bending and the resulting surface potential. A variety of SPV-based tools have been developed to make a wide range of measurements on semiconductors and dielectric films on top of semiconductors. For example, SPV measurements can be used to detect doping densities, characterize the degree of band bending or determine the density and position of electron energy states at semiconductor surfaces and interfaces. These systems sometimes include the ability to apply controlled amounts of charge to the surface of a dielectric film. While SPV systems come in a variety of configurations with a range of measurement capabilities, these systems are all similar in that they make measurements by either 1) applying charge or illumination to the surface and then measuring the resulting surface potential or change in surface potential using a vibrating Kelvin probe, or 2) positioning a stationary capacitive probe over the surface and varying the charge or illumination to generate a time-varying signal that can be detected by the capacitive sensor. In other words, these systems generate a signal by varying the probe-to-surface capacitance, the illumination intensity, or the charge on the surface. Like the Kelvin probe, SPV measurement systems are essentially point measurement systems, and are not suitable for the generation of high resolution, whole wafer images at production speeds.

A third type of system for inspecting and measuring surfaces utilizes a non-vibrating contact potential difference sensor. Like the vibrating Kelvin probe, the non-vibrating contact potential difference sensor consists of a conductive probe that is electrically connected to the semiconductor surface. The probe tip is positioned close to the surface to form a capacitor, and a potential difference is formed between the probe tip and the surface due to the difference in work functions or surface potentials. Unlike the Kelvin probe, however, the non-vibrating contact potential difference sensor does not vibrate perpendicular to the surface. Instead, the probe tip is translated parallel to the surface, or the surface is translated beneath the probe. Changes in the work function or surface potential at different points on the surface result in changes in potential between the surface and the probe tip. This causes a current to flow into the probe tip. This current is amplified and sampled to form a continuous stream of data that represents changes in potential across the surface. The non-vibrating contact potential difference sensor can acquire surface data at a much higher rate than the vibrating Kelvin probe because the signal is not formed by vibration of the probe, but is instead formed by the relative scanning motion between the probe and the surface. The non-vibrating contact potential difference sensor can provide a continuous stream of data at rates greater than 100,000 samples per second. High data acquisition rates permit high-resolution whole wafer images to be acquired in only a few minutes.

While the non-vibrating contact potential difference sensor is well-suited to high-speed imaging of wafer surface potential, it produces data on only two wafer surface characteristics—changes in surface potential and changes in surface height. For semiconductor inspection applications, the sensor is usually operated to minimize the height signal by minimizing variations in the height of the probe above the wafer surface or minimizing the average potential between the probe tip and wafer surface. As a result, the non-vibrating contact potential difference sensor typically produces data on one characteristic of a surface—changes in surface potential.

It would be desirable to expand the capabilities of the non-vibrating contact potential sensor so that it could measure additional wafer characteristics and discriminate between different types of non-uniformities. For example, doping uniformity is an important characteristic of a semiconductor which affects many fundamental and critical semiconductor characteristics. However, it is difficult to identify doping density variations using the contact potential difference signal because the effect of doping density on work function is reduced or altered by surface or interface states that induce band bending near the wafer surface. Also, doping density variations may be difficult to separate from other non-uniformities such as variations in surface chemistry and contamination. It would be useful to expand the capabilities of the non-vibrating contact potential difference sensor so that it could detect additional semiconductor characteristics, such as changes in doping density, and distinguish between different surface and bulk non-uniformities. In addition, it would be desirable to improve the sensitivity of the non-vibrating contact potential difference sensor so that it could detect smaller or more subtle non-uniformities.

SUMMARY OF THE INVENTION

The system and methods provide an enhanced non-vibrating contact potential difference sensor system that allows the sensor data to be used to detect bulk semiconductor non-uniformities, or to more easily detect and classify surface contaminants. Hereinafter, semiconductor material susceptible to inspection by the system herein described will be denoted generally as a "wafer". One embodiment includes a source of illumination that has variable intensity or spectrum of light output. The illumination source is used to illuminate the area under or near the non-vibrating contact potential difference sensor probe tip during scanning. In one embodiment, information on surface potential variations is acquired when the surface is illuminated with one or more illumination conditions that are optimized for the detection and classification of specific surface or bulk wafer characteristics that affect the response of the surface potential to illumination.

The apparatus consists of a non-vibrating contact potential difference sensor, a system for mechanically fixturing the wafer, a system for positioning the sensor a fixed distance above the wafer surface and generating relative motion between the probe tip and wafer surface such that the sensor probe tip moves parallel to the wafer surface, a source of illumination with variable intensity or spectrum of light that can irradiate the semiconductor wafer surface under or near the sensor probe tip, and a system for acquiring and processing the output signal from the sensor to identify and classify wafer non-uniformities.

One embodiment of operation shown in the flow diagram of FIG. 1b is as follows. First, a semiconductor wafer is placed and secured onto the fixture. The purpose of the fixture is to mechanically secure the wafer and to provide an electrical connection to the wafer surface. Because the non-vibrating contact potential difference sensor detects changes in surface potential, it is a time-varying signal. As a result, the contact between the fixture and wafer can be either capacitive or ohmic. The non-vibrating contact potential difference sensor probe tip is then positioned at a fixed height above the wafer surface. The wafer surface under or near the probe tip is illuminated with a specific intensity and spectrum of light and relative motion is generated between the probe tip and wafer surface such that the probe tip moves parallel to the wafer surface at a fixed height. As the probe tip moves over regions of the wafer surface with different surface potentials, the voltage between the probe tip and surface changes, resulting in a current into, or out of, the probe tip. This current is amplified and sampled to form a representation of variations in surface potential across the wafer. Optionally, the wafer may be scanned one or more additional times with different intensities or wavelengths of illumination to form additional representations of variations in surface potential. The resulting data from the one or more scans is then processed to identify and classify areas of wafer non-uniformity.

DETAILED DESCRIPTION OF THE PREFERRED EMBODIMENTS

The present invention provides an enhanced non-vibrating contact potential difference sensor 101 system that allows the sensor data to be used to detect bulk semiconductor non-uniformities, such as but not limited to variations in doping density, that may cause the surface potential to be sensitive to illumination level. This invention is not limited to the measurement of semiconductors with bare, clean surfaces. The chemical state of the surface may vary, or surface contamination may be present. Also, the wafer surface may be covered with a coating or film that permits illumination to penetrate through the film to the underlying semiconductor. For example, a silicon wafer surface is often coated with a silicon oxide film which is transparent to some wavelengths of illumination. This invention can be used to inspect a wafer covered with a film to detect defects in the underlying semiconductor or at the semiconductor-film interface. In addition, this invention can be used to detect or classify defects in, or on, the film that affect band bending in the semiconductor or the response of the semiconductor surface to illumination.

Figure 1A:
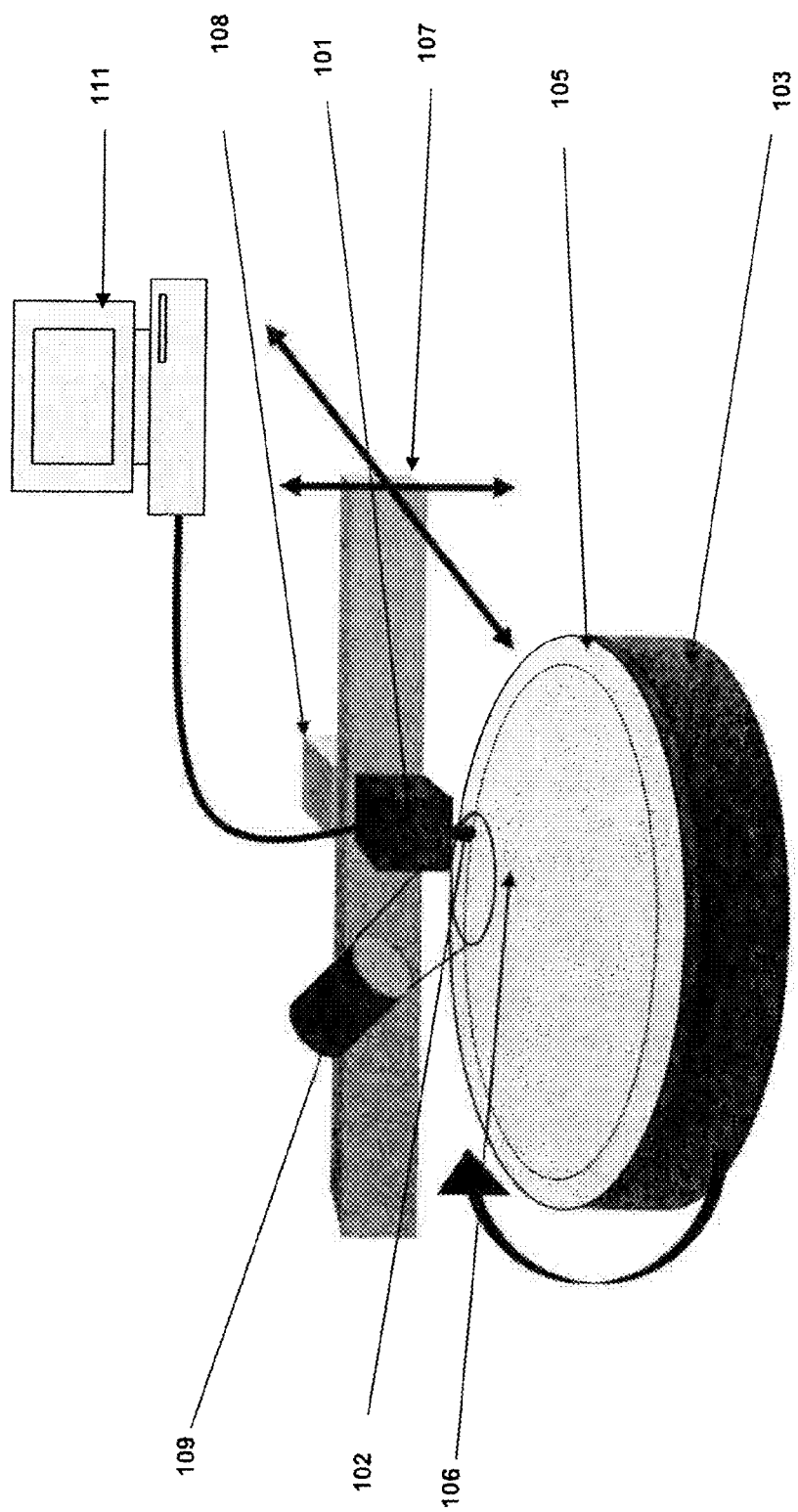
FIG. 1a is a diagram of wafer scanning system with a non-vibrating contact potential difference sensor and a source of controlled illumination and FIG. 1b shows a schematic flow diagram of operation of a preferred embodiment.
Figure 1B:
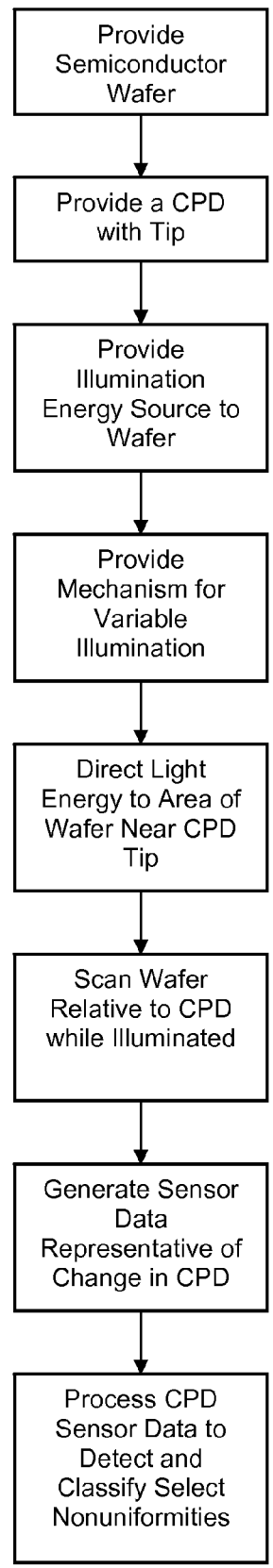

Referring to FIGS. 1a and 1b, the apparatus and method provides a non-vibrating contact potential difference sensor 101, a system 103 for mechanically fixturing the wafer 105, a system 107 for positioning the sensor 101 a fixed distance above the wafer surface 106 and generating relative motion between the probe tip 102 and wafer surface 106 such that the sensor probe tip 102 moves parallel to the wafer surface 106, a source of illumination 109 with variable intensity or spectrum of light that can irradiate the semiconductor wafer surface 106 under or near the sensor probe tip 102, and a system 111 for acquiring and processing the output signal from the sensor 101 to identify and classify wafer 105 non-uniformities.

In one embodiment, a semiconductor wafer 105 is placed on a conductive wafer fixture 103. This may be done manually or using an automated process such as, but limited to a wafer handling robot. The wafer 105 is held in place such as by using vacuum. Alternative methods of holding the wafer 105 include, but are not limited to, electrostatic forces and edge gripping. In one embodiment, the fixture 103 is mounted to a spindle which can rotate the wafer 105 about its center. The non-vibrating contact potential difference sensor 101 is attached to a positioning system 107 that can adjust the height of the sensor 101 above the wafer surface 106 and can move the sensor 101 radially from at least the center of the wafer 105 to one edge of the wafer 105. The non-vibrating contact potential difference sensor 101 is electrically connected to the wafer surface 106 via the conductive wafer fixture 103. This connection can be resistive or capacitive. In one embodiment, a height sensor 108 that has been calibrated to the height of the non-vibrating contact potential difference sensor probe tip 102 is also mounted on the same positioning system 107 as the non-vibrating CPD sensor 101.

A light source 109 with variable intensity or variable wavelength is also mounted on the positioning system at an angle such that the illuminated area includes at least the area next to the non-vibrating contact potential difference sensor probe tip 102, with the illuminated area extending beneath the probe tip 102 to the extent allowed by the gap between the probe tip 102 and the wafer 105 and the angle of the light beam. The light source 109 can be a laser, incandescent lamp or other light source. A broadband light source may be coupled with a variable optical filter for selecting the desired wavelength and intensity of illumination. The non-vibrating contact potential difference sensor probe tip 102 may be transparent to illumination wavelengths to facilitate the illumination of the wafer surface 106 beneath the probe tip 102. Alternately, the probe tip 102 may be shaped to facilitate illumination of the wafer surface 106 beneath the probe. The precise size and position of the illuminated spot is set so that the non-vibrating contact potential difference sensor 101 will scan over the illuminated area, which may include all or a large part of the wafer surface 106. If the light source 109 illuminates the entire wafer surface 106, or if it illuminates the entire area traversed by the sensor probe tip 102 during the scanning operation, then the light source 109 can be mounted in a fixed location and not on the positioning system 107.

After the wafer 105 is secured to the fixture, the height sensor 108 is positioned above one or more points on the wafer surface 106 and the height of the wafer surface 106 is measured. These wafer height measurements are used to calculate the position of the non-vibrating contact potential difference sensor 101 that will produce the desired distance between the probe tip 102 and the wafer surface 106. This information is used to position the probe tip 102 at a fixed height above the wafer surface 106, and the probe tip 102 is moved to a point above the outside edge of the wafer 105. Illumination is enabled and the appropriate intensity and wavelength are selected for the inspection application. For example, if the application is the detection of doping density, then a high intensity of super-bandgap illumination may be selected. If the application is surface contamination detection, then the intensity and wavelength appropriate for the likely contaminants are selected.

The probe 101 is held stationary and the wafer 105 is rotated on the spindle such that the probe tip 102 moves above the wafer 105 along a circular path that is centered at the wafer 105 center. Data is acquired during a single rotation of the wafer 105. The sensor 101 is then moved a programmable distance along the radius of the wafer 105 towards the wafer center. Another rotation of data is acquired at this new radius. The probe tip 102 continues to step and scan concentric circular regions of the wafer 105 until the probe reaches the wafer center. The resulting data is then assembled into an image of the wafer 105. Alternately, each concentric circular region of the wafer 105 could be scanned multiple times and the resulting data averaged to reduce the effect of random noise. This image is processed to identify and classify non-uniformities. This processing can take many forms. It may be as simple as the thresholding of signal values to detect regions of the wafer surface 106 where the surface potential is changing relatively rapidly. The differential sensor data can also be integrated to generate an image which represents relative surface potential values. This integrated image can also be processed or thresholded to identify regions of high or low potential.

Figure 2:
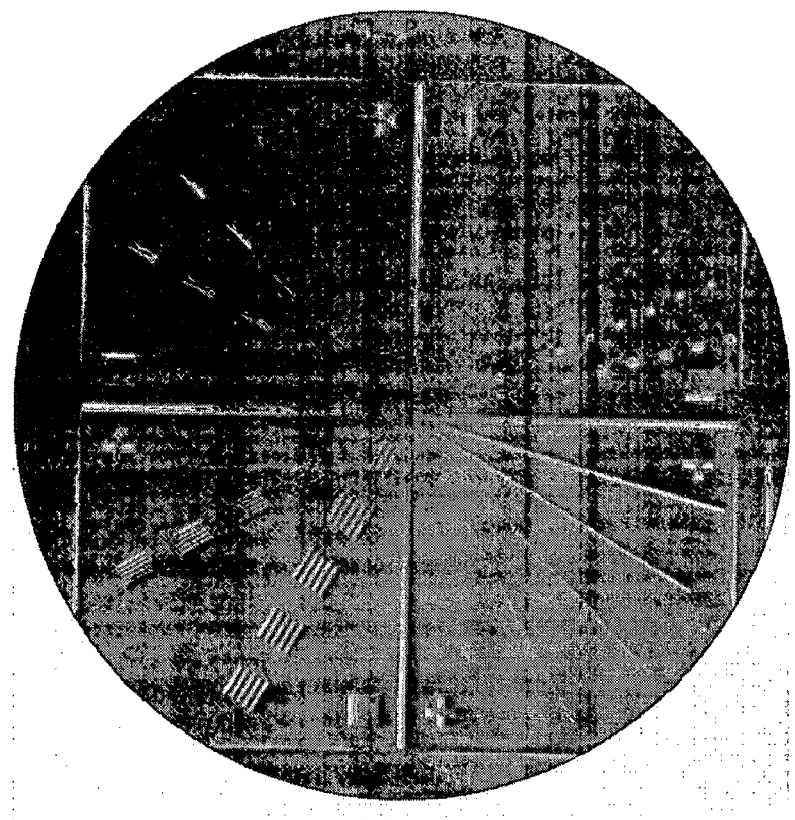
FIG. 2a is a diagram of radial scanning operation.
FIG. 2b illustrates a sample image from such a scanning operation.
Figure 2:
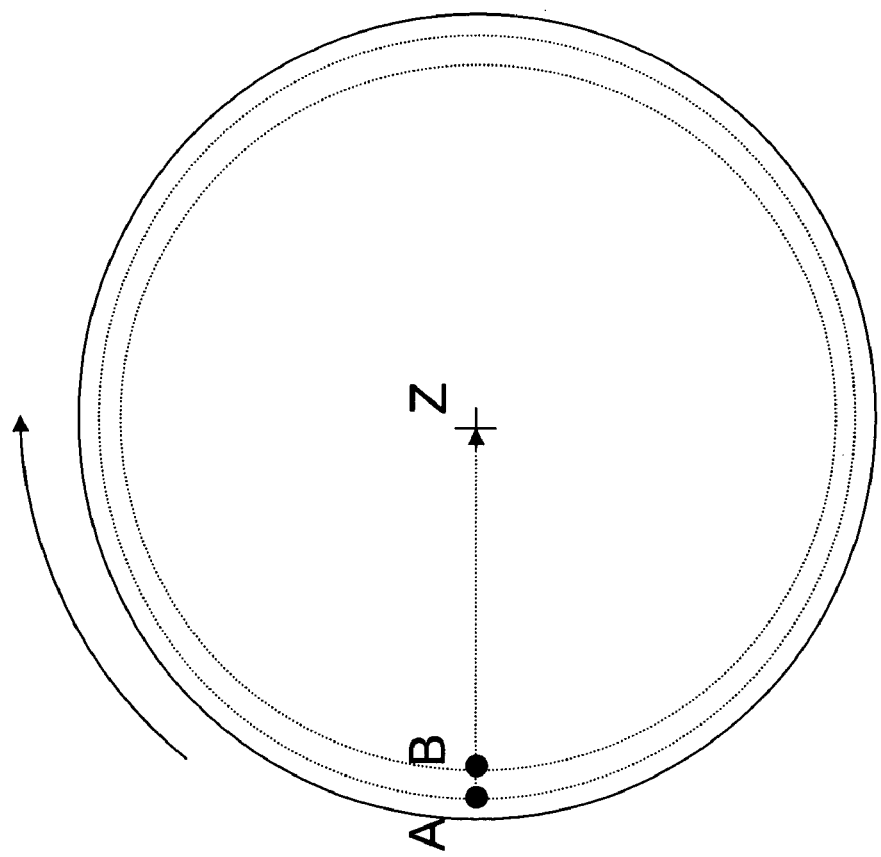

FIG. 2 illustrates a diagram of the radial scanning of one embodiment of the present invention. The non-vibrating contact potential difference sensor probe tip 102 is positioned at point "A" near the edge of the wafer 105. The wafer 105 is rotated on the wafer fixture 103 and a circular track of data is scanned. The probe tip 102 is moved a programmable distance towards the wafer 105 center to point "B" and a second circular track of data is scanned. This process is repeated until the probe tip 102 reaches the center of the wafer 105. The resulting data is combined into an image of the wafer surface 106. A sample image is shown as FIG. 2b.

One aspect of the invention relates to the detection of variations in doping density or bulk contamination in a semiconductor. Variations in doping density or bulk contamination can affect the Fermi level of the semiconductor, and the Fermi level directly affects the work function. However, band bending at the surface of the semiconductor may reduce the effect of Fermi level variations on work function changes. In one embodiment, the wafer 105 may be illuminated with super bandgap illumination to reduce this band bending effect. The wafer surface 106 is then scanned using the non-vibrating contact potential difference sensor 101 to obtain data on surface potential and Fermi level changes across the wafer 105. The resulting data is processed to detect these variations which represent variations in doping density. Alternatively, the wafer 105 could be scanned with two different intensities of super-bandgap illumination, where one of the intensities might be 0, and the difference of the two scans calculated. This difference data could then be used to detect areas with different levels of band bending which would indicate variations in doping density. The non-vibrating contact potential difference sensor signal generated by other types of non-uniformities that don't affect band bending would not be sensitive to illumination. The signal from these types of non-uniformities would be eliminated by taking the difference of data generated with two different illumination intensities.

A second aspect of this invention is the identification or classification of surface chemistry or contamination based on the effect of super bandgap illumination on surface work function. The effect of a fixed intensity of super bandgap illumination on the amount of band bending, and consequently its effect on work function, is dependant on the density and distribution of surface electron energy states that exist within the bandgap. These states are created by the termination of the semiconductor bulk at the surface, the reconfiguration of the semiconductor surface, molecules or atoms that chemically bond to the wafer surface 106 or molecules or atoms that adsorb on the wafer surface 106. Different surface conditions, such as hydrogen termination or oxide termination, different surface contaminants or adsorbed molecules, or dielectric films deposited on the surface of the wafer will generate different densities or distributions of surface states. Variations in surface state can result in variations in the magnitude of band bending at the surface. This invention permits the wafer surface 106 to be measured using the non-vibrating contact potential difference sensor 101 with an intensity of super bandgap illumination selected to maximize the difference in work function of the surface for contaminated and uncontaminated regions of the wafer 105, or to maximize the difference in work function of the surface between two different contaminants. In addition, the surface can be measured two or more times using different intensities of illumination that maximize the change in surface potential for contaminated or uncontaminated regions, or regions with different contaminants. The differences between these measurements can then be used to detect contaminants or classify different contaminants or surface conditions.

A third aspect of this invention is the detection and classification of surface chemistry or contamination based on the effect of sub-bandgap illumination on surface work function. Sub bandgap illumination lacks sufficient energy to cause valence band electrons to jump directly to the conduction band. However, it can cause transitions from the valence band to a surface state or from a surface state to the conduction band. Illumination of the surface with sub-bandgap illumination of varying wavelengths can be used to populate and depopulate these gap states, resulting in changes in surface potential and work function. The change in surface potential with varying wavelengths of illumination is dependant on the surface condition and chemistry. This invention permits the wafer surface 106 to be measured using the non-vibrating contact potential difference sensor 101 with a wavelength of sub bandgap illumination selected to maximize the difference in work function of the surface for contaminated and uncontaminated regions of the wafer 105, or to maximize the difference in work function of the surface between two different contaminants. In addition, the surface can be measured two or more times using different wavelengths of illumination that maximize the change in work function for contaminated or uncontaminated regions, or regions with different contaminants. The differences in these measurements can then be used to detect contaminants or classify different contaminants or surface conditions.

The wafer 105 may be scanned more than once, where the wavelength or intensity of illumination is altered between each scan. These scans can then be combined, for example by taking the difference, and the resulting data, processed to identify and classify surface or bulk non-uniformities. Scanning with two or more illumination conditions can be done by scanning the whole wafer 105 with one type of illumination, then changing the illumination and scanning the whole wafer 105 again, or it can be accomplished by scanning a single concentric circular path of data using one illumination condition, changing the illumination, rescanning the same path with the new illumination condition, and then repeating for all circular paths at each radius.

In addition, the intensity or wavelength of the illumination can be changed during the scanning operation. For example, the illumination can be switched on and off so that the varying illumination causes a change in surface potential at the switching frequency. The switching operation can be implemented by using an optical chopper that passes the illumination through a spinning disk with an alternating pattern of transparent and opaque features. The resulting illumination-induced surface potential signal can be separated from the signal created by the lateral motion of the non-vibrating contact potential difference sensor 101 relative to the wafer 105 by applying a frequency bandpass filter that passes the signal only at the switching frequency.

If the wafer surface is covered with a dielectric film, then the film surface can be charged with ions prior to measurement. The ions can be created via corona discharge or some other comparable method. Charging of the film surface can be used to bias the surface of the semiconductor into accumulation, depletion or inversion, which will affect band bending and SPV. This biasing charge can be applied and maintained at a constant level for all measurements, or it can be altered between sequential scans of the same wafer surface.

In one embodiment, the angle that the illumination energy contacts the wafer surface maybe controlled to provide for a desired depth of penetration into the wafer surface.

EXAMPLES

Figure 3:
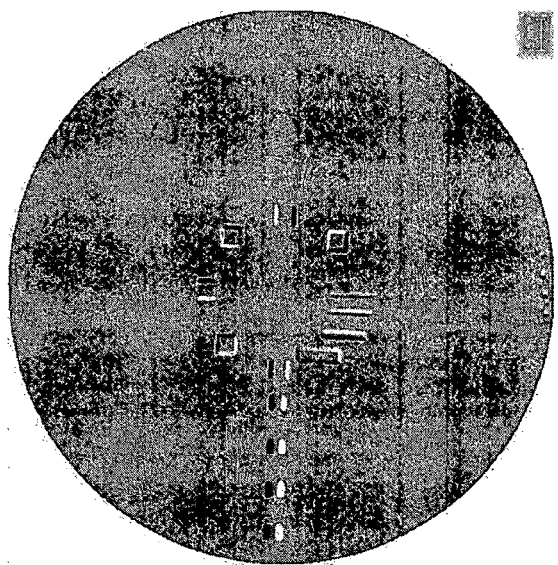
FIG. 3 illustrates non-vibrating contact potential difference images of a wafer with (a) super-bandgap illumination, (b) no illumination and (c) difference between FIGS. 3(a) and 3(b)
Figure 3:
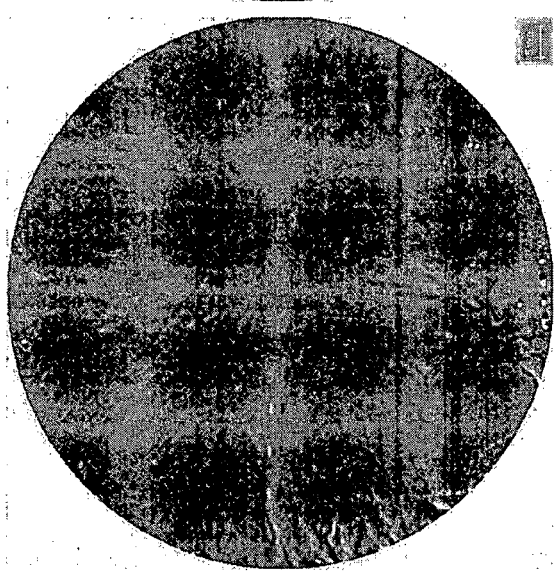
Figure 3:
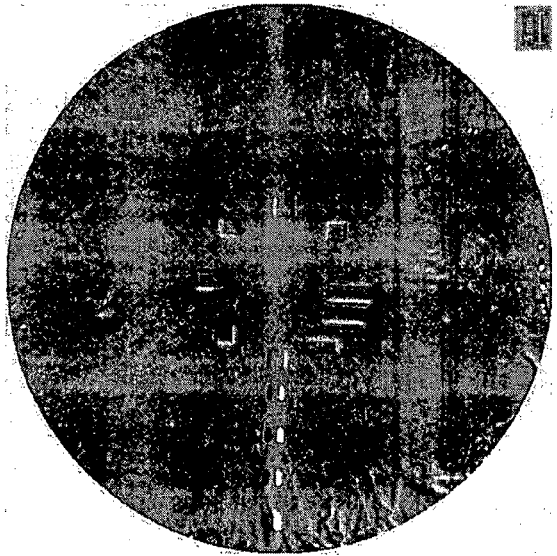

FIG. 3 illustrates non-vibrating contact potential difference images of a wafer 105. FIG. 3(a) is super-bandgap illumination, FIG. 3(b) is with no illumination and FIG. 3(c) is the difference between that shown in FIG. 3(a) and FIG. 3(b). The pattern in 3(c) is boron implanted into the wafer 105. The difference image shows a strong doping pattern and minimizes the signal from surface contaminants which are visible in (a) and (b).

Figure 4:
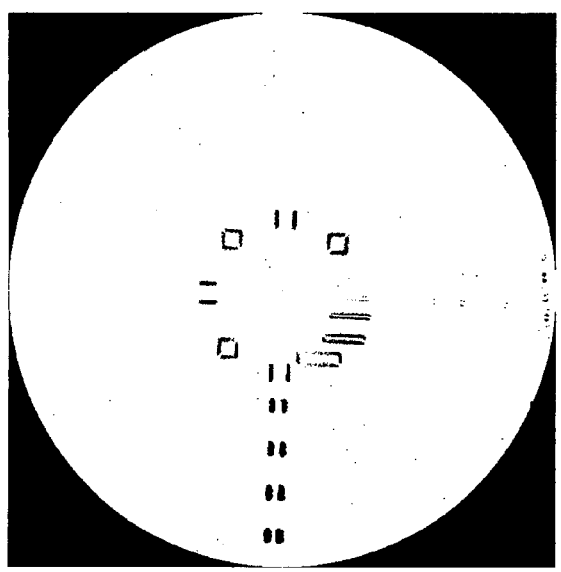
FIGS. 4(a)-(c) illustrates non-vibrating contact potential difference images of the wafer shown in FIG. 3(a)-(c) with processing to identify regions of non-uniformity.
Figure 4:
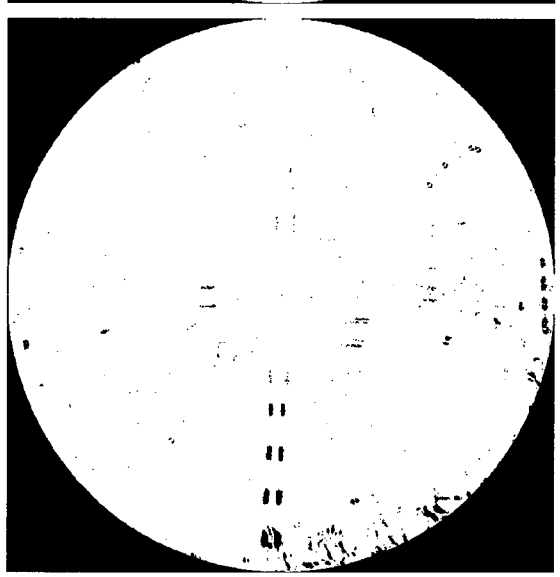
Figure 4:
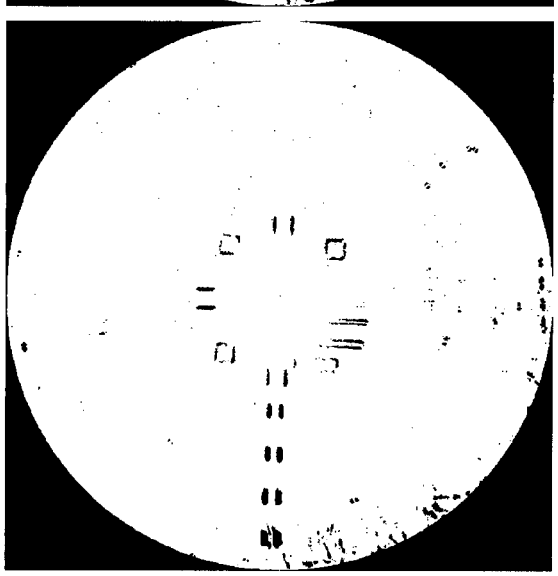

FIG. 4 illustrates the non-vibrating contact potential difference images of the wafer 105 shown in FIGS. 3(a)-(c) with processing to identify regions of non-uniformity. The images have been processed by identifying regions of the image that fall above and below threshold values. Non-uniformity is clearly identified in FIG. 4(c), but is not distinguished from surface contamination in FIGS. 4(a) and 4(b).

There are many alternate mechanical configurations and scanning operations that would accomplish the same result as the embodiment described above. For example, the non-vibrating contact potential difference sensor 101, height sensor 108 and illumination source 109 could all be mounted at fixed locations, and the wafer 105 could be moved and rotated beneath these stationary elements. Instead of stepping from one radius to the next, the non-vibrating contact potential difference sensor 101 could be moved continuously along the wafer 105 radius while the wafer 105 is spinning to create a continuous stream of data that spirals across the whole surface of the wafer 105. Also, instead of the radial scanning operation described above, the non-vibrating contact potential difference sensor 101 could be moved linearly across the wafer 105 in a back-and-forth manner to scan the entire wafer surface 106. Also, multiple non-vibrating contact potential difference sensors and illumination sources could be used to acquire multiple measurements simultaneously to reduce the time required to measure a wafer.

The foregoing description of embodiments of the present invention have been presented for purposes of illustration and description. It is not intended to be exhaustive or to limit the present invention to the precise form disclosed, and modifications and variations are possible in light of the above teachings or may be acquired from practice of the present invention. The embodiments were chosen and described in order to explain the principles of the present invention and its practical application to enable one skilled in the art to utilize the present invention in various embodiments, and with various modifications, as are suited to the particular use contemplated.

What is claimed is:

1. A method of detecting non-uniformities of a semiconductor wafer, comprising the steps of:
    providing a semiconductor comprising a wafer having a wafer surface;
    providing a contact potential difference sensor having a probe tip;
    providing a source of illumination energy in communication with the wafer surface;
    providing a mechanism providing variable illumination;
    directing the illumination energy at an area of the wafer surface that includes a sampling area located in proximity with the contact potential difference sensor probe tip;
    scanning the wafer surface laterally relative to the contact potential difference sensor while the surface of the semiconductor is illuminated;
    generating sensor data representative of changes in the contact potential difference between the sensor probe tip and the wafer surface as the sensor probe tip scans laterally across the wafer surface; and
    processing the contact potential difference sensor data to detect a pattern that represents a non-uniformity,
    wherein the non-uniformity is selected from the group consisting of chemical non-uniformities, physical non-uniformities, electrical non-uniformities, and combinations thereof.

2. The method of claim 1, wherein the variable illumination energy comprises at least one of a varying intensity, varying light spectrum, and varying angle of input to the wafer surface.

3. The method of claim 1 wherein the illumination energy comprises wavelength(s) of light with energies that are greater than a band gap of the semiconductor wafer.

4. The method of claim 1 wherein the illumination energy comprises wavelength(s) of light with energies that are less than a band gap of the semiconductor.

5. The method of claim 1 wherein the non-uniformity comprises a variation in semiconductor doping density.

6. The method of claim 1 wherein the non-uniformity comprises a contaminant in the semiconductor.

7. The method of claim 6 wherein the contaminant comprises a metal or organic contaminant on the wafer surface of the semiconductor.

8. The method of claim 1 wherein the non-uniformity comprises a variation in surface chemistry.

9. The method of claim 1 wherein the source of illumination energy comprises a laser.

10. The method of claim 1 wherein the probe tip of the contact potential difference sensor is transparent to wavelengths of illumination energy.

11. The method of claim 1 wherein the probe tip of the contact potential difference sensor is shaped to allow illumination of the area under the probe tip.

12. The method of claim 1 wherein the semiconductor comprises a covering of a film that is transparent to at least some wavelengths of illumination energy.

13. The method of claim 12 wherein the defect comprises charging on or in the transparent film.

14. The method of claim 1 further including the steps of scanning the wafer surface at least twice where the spectrum or intensity of illumination energy is changed between scans; and processing the contact potential difference sensor data from the multiple scans to detect a pattern that represents a defect.

15. The method of claim 14 wherein the processing of the contact potential difference sensor data includes calculating the difference between the results of one scan and the results of a second scan, where the two scans were taken with different illumination conditions.

16. A system for detecting non-uniformities of a semiconductor wafer, comprising:
    a semiconductor mounting surface adapted to receive a semiconductor wafer having a wafer surface;
    a contact potential difference sensor having a probe tip and positionable adjacent to the mounted semiconductor wafer, the sensor and the semiconductor wafer movable relative to each other;
    a source of illumination energy in communication with the surface, the source of illumination energy providing directable and variable illumination energy;
    the sensor generating contact potential difference data as the sensor probe tip scans laterally across the semiconductor surface while an area of the wafer surface that includes a sampling area located in proximity with the contact potential difference sensor probe tip is illuminated by the illumination source of illumination energy; and
    a processor for receiving the contact potential difference sensor data from the sensor and processing the data to detect a pattern that represents a non-uniformity.

17. The system of claim 16, wherein the non-uniformity is selected from the group consisting of chemical non-uniformities, physical non-uniformities, electrical non-uniformities, and combinations thereof.

18. The system of claim 16, wherein the illumination energy has a varying intensity, varying spectrum and varying angle of input to the wafer surface.

19. The system of claim 16 wherein the illumination energy contains wavelength(s) of light with energies that are greater than a band gap of the semiconductor.

20. The system of claim 16 wherein the illumination energy comprises wavelength(s) of light with energies that are less than a band gap of the semiconductor.

21. The system of claim 16 wherein the non-uniformity comprises a variation in semiconductor doping density.

22. The system of claim 16 wherein the non-uniformity comprises a contaminant in the semiconductor.

23. The system of claim 22 wherein the contaminant comprises a metal or organic contaminant on the wafer surface of the semiconductor.

24. The system of claim 16 wherein the non-uniformity comprises a variation in surface chemistry.

25. The system of claim 16 wherein the source of illumination energy comprises a laser.

26. The system of claim 16 wherein the probe tip of the contact potential difference sensor is transparent to wavelengths of the illumination energy.

27. The system of claim 16 wherein the probe tip of the contact potential difference sensor comprises a shape to allow illumination of the area under the probe tip.

28. The system of claim 16 wherein the semiconductor comprises a covering film that is transparent to at least some wavelengths of illumination energy.

29. The system of claim 28 wherein the defect comprises charging on or in the transparent film.

* * * * *